(12) United States Patent
Toblesky et al.

(10) Patent No.: US 6,255,047 B1
(45) Date of Patent: Jul. 3, 2001

(54) BIOSYNTHETIC CARBOHYDRATE-DEFICIENT TRANSFERRIN REFERENCES

(75) Inventors: Kristen Toblesky, Yorba Linda; Douglas Kang, Mission Viejo; Alireza Ebrahim, Foothill Ranch; Eric Vanderslice, Fullerton, all of CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 09/514,827

(22) Filed: Feb. 28, 2000

(51) Int. Cl.$^7$ .......................... C12Q 1/00; G01N 33/53; A01N 1/00
(52) U.S. Cl. ..................... 435/4; 435/7.1; 435/2
(58) Field of Search .................. 435/2, 15, 193, 435/14, 7.1, 775, 4; 436/87, 164, 172

(56) References Cited

U.S. PATENT DOCUMENTS

| 4,379,087 |   | 4/1983  | Coan et al. |         |
|-----------|---|---------|-------------|---------|
| 5,352,616 | * | 10/1994 | Sundrehagen et al. | 436/501 |
| 5,432,059 | * | 7/1995  | Bean et al. | 435/15  |
| 5,798,212 |   | 8/1998  | Sundrehagen . |       |
| 5,798,267 |   | 8/1998  | Harasymiw . |         |
| 5,823,196 |   | 10/1998 | Harasymiw . |         |

OTHER PUBLICATIONS

I. Kwoh–Gain et al., *Clin. Chem.* (1990) 36(6):841845.
H. Stibler et al., *Acta. Med. Scand.* (1979) 206:275–281.
K. Viitala et al., *Clinical Chemistry* (1998) 44(6):1209–1215.
Cohn et al., "Preparation and properties of serum and plasma proteins, IV. A System for the separation into fractions of the protein ad lipoprotein components of biological tissues and fluids," *J. Am. Chem. Soc.* (1946) 68:459–475.

\* cited by examiner

*Primary Examiner*—Jon P. Weber
*Assistant Examiner*—Patricia A. Patten
(74) *Attorney, Agent, or Firm*—Townsend and Townsend and Crew LLP

(57) ABSTRACT

References, i.e., solutions of known concentration for use as controls, calibrators, or standards, for assays of carbohydrate-deficient transferring in bodily fluids are obtained from units of bodily fluids from normal healthy individuals by digesting the transferring in these units with exogenous neuraminidase to achieve concentrated CDT solutions, which are then added in preselected proportions to a base matrix to achieve target concentrations.

17 Claims, 1 Drawing Sheet

BIOSYNTHETIC CARBOHYDRATE-DEFICIENT TRANSFERRIN REFERENCES

BACKGROUND OF THE INVENTION

1. Field of the Invention

This invention relates to reference solutions for use as supplementary components of diagnostic tests performed on serum and other bodily fluids for chronic overconsumption of alcoholic beverages.

2. Description of the Related Art

Diagnostic methods for the detection of alcoholism and alcohol abuse are useful in prescribing treatment to individuals suffering from these conditions and are an important tool in lessening the attendant health complications and the societal consequences that often result. The diagnostic methods consist of determining the level of one or more species in the subject's bodily fluid that serve as biochemical markers for chronic or excessive alcohol consumption. These markers are γ-glutamyltransferase (GGT), aspartaie aminotransferase (AST), alanine amino transferase (ALT), and carbohydrate-deficient transferring (CDT). Studies have shown that the last of these assays is particularly sensitive and has greater specificity for the condition than the others.

The term "carbohydrate-deficient transferring" or "CDT" refers to certain isoforms of transferring that are formed by conversion of transferring and are present in elevated concentration in the bodily fluids of chronic alcohol abusers. Transferring itself (i.e., normal or intact transferring), which is the iron-transporting protein in blood, is a glycoprotein with two N-linked polysaccharide (or carbohydrate) chains, each of which contains either two or three branches. Each branch is terminated with a sialic (N-acetylneuraminic) acid residue. Transferring exists in a variety of isoforms, differing in the number of polysaccharide chains and the number of branches on each chain. Five such isoforms have been identified by electrochemical separation means based on differences in their pI. The higher the pI, the fewer the polysaccharide chains (and the fewer the sialic acid residues) on the molecule. The major isoform is one that has a pI of 5.4, while those that are elevated in subjects that are chronic alcohol abusers are those having pI's of 5.7 or greater. Thus, the term "carbohydrate-deficient transferrin" or "CDT" refers to transferring isoforms whose pI is 5.7 or greater. (The terms "desialylated transferrin" and "dTf" are also used to denote the same isoforms.) The CDT fraction in normal subjects is less than 0.8% of the total transferring, and can rise to as much as ten times that amount in alcohol abusers.

Diagnostic tests for CDT typically begin with the separation of CDT from intact transferring by ion-exchange chromatography. Quantitation of the CDT in the eluate is then achieved by either radioimmunoassay or turbidimetric measurement. Other methods involve the use of high-performance liquid chromatography (HPLC), isoelectric focusing, or immunoblotting in place of ion-exchange chromatography. In each case a reference is needed to check the condition of the assay components, to monitor the precision and accuracy of the method, or to translate the test result to an numerical figure representing the CDT level (i.e., to calibrate the test). To be effective, the reference should be as sensitive as an actual patient sample to the analytical variances that are encountered in the typical clinical laboratory. The reference should also be stable over long periods of time so that it can be stored until ready for use.

The term "reference" is used throughout this specification to denote any fluid composition containing CDT at a known and preselected concentration. Solutions of known concentrations are useful for a variety of purposes. One use is as a control for purposes of determining that a particular test kit or apparatus, or components of the test kit, have not deteriorated during shipping, storage, or handling and are functioning in the intended manner. Another use is as a standard for calibration or for verification of the linearity of the test response for translating test readings into numerical values for percent CDT. Whether the reference serves as a control or a standard, it is often useful to have two or more such references at different CDT levels. When used as controls, one reference may have a CDT level in the range of a healthy subject and another in a range representing an alcohol abuser. When used as calibrators, multiple references are useful in bracketing the ranges and particularly the threshold value that differentiates normal patients from those suffering from alcohol abuse.

Methods of preparing references exist in the prior art. These involve either screening the plasma or serum from blood donors to identify units with CDT levels in the target ranges, or isolating and separating CDT from units of normal concentration and using the separated CDT to spike a base matrix such as human serum. Both approaches are time-consuming and costly. The former requires extensive testing and may not produce sufficient amounts of the reference for commercial use. The latter entails labor-or capital-intensive chemical separation techniques including dialysis, precipitation, electrophoresis, and chromatography. As a result, purified CDT is presently available from commercial suppliers only at high cost. The present invention is directed to satisfying the need of supplying CDT reference solutions at low cost for use for any of the purposes described above, with high reproducibility from lot to lot and with ease of manufacturing.

SUMMARY OF THE INVENTION

It has now been discovered that a reference for use as a control or a standard for CDT assays having the characteristics listed above, and preferably a set of such references, can be prepared by digesting transferring in a unit of bodily fluid with a ineuraminidase to convert at least a substantial portion of the intact transferring in the fluid to CDT. Following the conversion, the enzyme is removed and the concentration of the CDT is adjusted by dilution of concentration if either necessary or desired, and the resulting CDT solution is used to spike (i.e., to add concentrated CDT to) a base matrix to form the reference. The conversion of the intact transferring proceeds in a surprisingly efficiently manner with no effect on other components of the bodily fluid that might interfere with or obscure the indications of the CDT level. References prepared in this manner are surprisingly reproducible and stable, retaining the CDT level thus achieved without reversion back to the undigested isoforms despite the presence of the other hydrolysis products in the same solution. These and other features, objects and advantages of the invention are explained in more detail below.

DETAILED DESCRIPTION OF THE INVENTION AND SPECIFIC EMBODIMENTS

Figure 1:
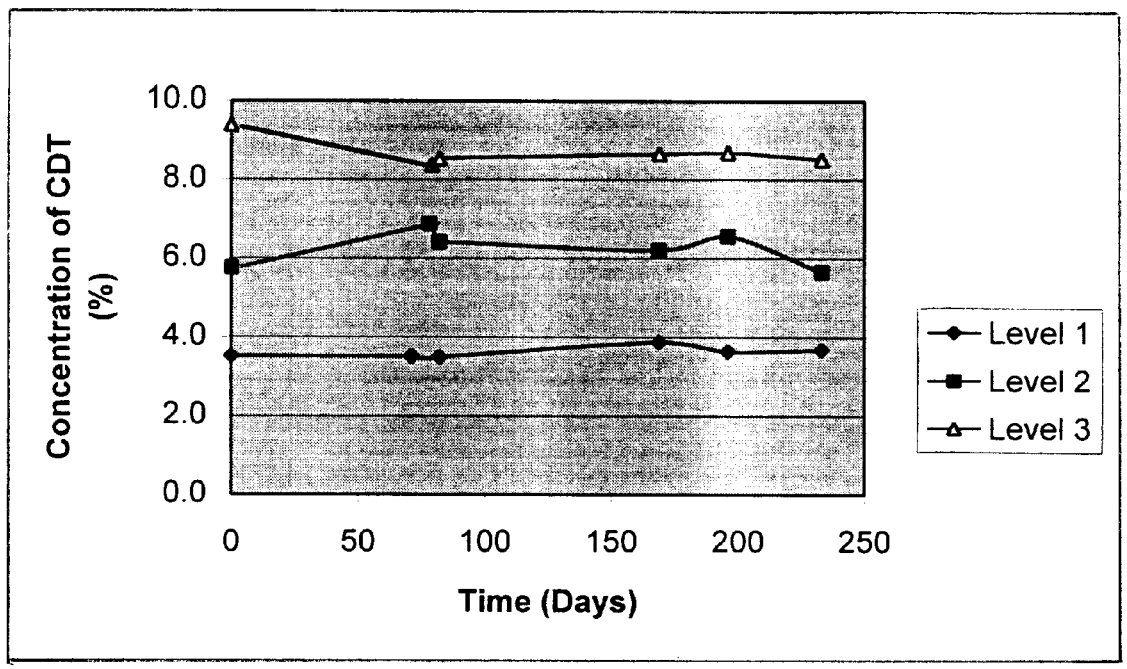
FIG. 1 is a plot of measured percent CDT concentration as a function of time for three CDT reference solutions prepared in accordance with this invention, the plot providing an indication of the stability of the solutions in closed vials.

Suitable starting materials for this invention are human bodily fluids that contain transferring of which a substantial portion is intact transferring or the transferring isoforms that are prevalent in healthy individuals, i.e., isoforms with pI values below 5.7, and most typically 5.4 and below. Fluids taken from healthy individuals are particularly convenient and are entirely suitable. These fluids include whole blood, plasma, scrum, and cerebrospinal fluid. Fractions of these fluids in which the proportions of transferring relative to other proteins are higher than those of the whole fluids may be used as well, and are in fact preferred. Plasma and serum, and particularly fractions thereof, are preferred.

When a fraction of a bodily fluid is used, the fraction may be obtained by conventional techniques that are known in the art, and suitable fractions are available from commercial suppliers in the biochemical industry. Preferred fractionation methods are the Cohn ethanol fractionation technique and its modifications. Descriptions of this technique are found in Cohn, E. J., el al., "Preparation and Properties of Serum and Plasma Proteins. IV. A System for the Separation into Fractions of the Protein and Lipoprotein Components of Biological Tissues and fluids," *J. Am. Chem. Soc.* 68:450–475 (1946), and in U.S. Pat. No. 2,390,074, issued Dec. 4, 1945, to Cohn, E. J. The contents of these documents are incorporated herein by reference. The various Cohn fractions, known in the art by Roman numerals, are pastes of partially precipitated proteins, and successive fractions are obtained by a gradual lowering of pH and a gradual increase in the amount of ethanol added to the fraction. The preferred transferring-containing fraction for use as a starting material in the present invention is the fraction known as Fraction IV, separated under conditions including a pH of approximately 5.8 and the presence of ethanol at a mole fraction of approximately 0.163.

The fluid once obtained may be processed further to render it more suitable for transferring digestion. When a Cohn fraction is used, for example, the fluid may be dialyzed to remove the ethanol that was used in the fractionation. Conventional dialysis methods can be used. It is also advantageous in many cases to concentrate the transferring in the solution, which is also readily achievable by dialysis and other conventional methods. Preferred solutions are those in which the transferring concentration is at least about 300 mg/dL, and most preferred are those in which the transferring concentration is at least about 1,000 mg/dL.

Neuraminidase from any biological source can be used. Species of the genus Clostridium are examples of such a source, particularly *Clostridium perfringens*. Other sources are *Arthrobacter ureqfaciens, Salmonella typhimuirium, Vibrio cholerae*, Streptococcus sp., and *E. coli*. The digestion is performed under conditions that are suitable for typical enzyme digestion, and preferably those that result in optimal enzyme activity. Since the enzymes are known, the conditions at which each enzyme displays optimal activity will be known or readily determinable to those skilled in the use of enzymes. In general, a temperature in the vicinity of physiological temperature and a pH in the range of from about 4.5 to about 5.5 are currently believed to produce the best results. In general, the digestion conditions and the time allowed for digestion are selected to achieve transferring isoforms of which at least a majority (by weight) are CDT. Preferably, the CDT in the solution after digestion amounts to least about 75% by weight of the total transferring in the solution, and most preferably at least about 85% by weight.

A convenient way to facilitate the removal of enzyme from the CDT solution once the digestion step is completed is to use an enzyme that is immobilized on a solid support of inert material that remains insoluble in, and can thus be easily separated from, the processing liquids. Immobilization of the enzyme is readily achieved by covalent bonding. One example of a solid support is the wall of a reaction vessel such as a test tube or a well of a multi-well plate. Separation of the CDT solution from enzyme immobilized on such a support is achieved by simply extracting the liquid from the test tube or well. Another example is a permeable membrane or pad. Digestion may be achieved by circulation of the fluid through the membrane or pad, and separation may be achieved by simply removing the membrane or pad from the circulating fluid. A third example, and one that is preferred, are beads or particles, particularly those that are microscopic in size. Examples of bead materials are ethylene maleic anhydride, polyacrylamides, polystyrene and derivatives, nylon, silicone rubber, latex, cellulose, starch, agarose, dextran, and derivatives of each of the foregoing, as well as silica glass beads, metals, and metal oxides. Enzymes immobilized on microscopic beads are available from commercial suppliers of materials to biochemical laboratories. Digestion is achieved by forming a slurry of the beads in the fluid to be digested, and incubating the slurry for a suitable period of time under appropriate conditions of temperature and pH. Separation is then achieved by centriftigation, filtration, decantation, or any other conventional means of separating solids from a suspension or dispersion. While processes of this type are batch processes, continuous processes may also be used. For example, the fluid to be digested can be passed on a continuous basis through a column containing a packed bed of enzyme-coated beads, with the fluid emerging in digested form from the column.

Once the CDT solution is recovered, aliquots are added to quantities of a base matrix to serve as references of the chosen CDT levels. The base matrix may be any fluid that can be used in an analytical procedure or instrument in the same manner that bodily fluids are used for CDT assays. Examples include the same types of fluids that are used as sources of traisferrin for digestion in the first stages of the method of this invention, i.e., blood, serum, plasma and cerebrospinal fluid. Artificial or simulated versions of these fluids can also be used. The proportions of CDT solution and base matrix are selected to achieve references having the desired target concentrations. Preferably, a set of two or more references are prepared in this manner, with graduated levels of CDT that span or bracket the CDT levels that are typically indicative of alcohol abuse.

Once the references are prepared at the appropriate concentrations, conventional antimicrobial agents, stabilizing agents, or both can be added to improve the shelf life and reliability of the references. Examples of suitable antimicrobial agents are sodium azide and antibiotics such as ciprofloxacin. The stabilizing agents will serve to prevent oxidation of the CDT or any other transferring isoforms present in the standards or degradation to smaller degradation products. Mild reducing agents may be used as stabilizing agents, or the compositions may be stored in an atmosphere of inert gas such as argon to reduce their susceptibility to oxidation.

The following examples are offered for purposes of illustration, and are not intended to limit the scope of the invention.

EXAMPLES

1. Preparation of Transferring Solution

A 20% (weight/volume) solution of Cohn Fraction IV human paste solution (200 g, Baxter Hyland Corporation, Deerfield, Ill., USA) was prepared in 50 mM Tris buffer (1,000 mL) with pH of 8.0. Insoluble matter was settled by centrifuge. and the supernatant transferring solution was filtered through a 0.45-micron filter. The transferring solution was then dialyzed against two volumes of Tris buffer (50 mM, pH 8.0) to remove alcohol. The dialyzed transferring solution was then assayed for its transferring content by a conventional assay (Beckman Array, Beckman Coulter, Inc., Fullerton, Calif., USA), and concentrated to about three times its original concentration by further dialysis to achieve a transferring concentration above 1,000 mg/dL. The pH of the solution was then adjusted to 5.0 with 5N HCl.

2. Conversion of Transferring to CDT

Agarose beads with neuraminidase from *Clostridiun perfringes* bonded to the surface (obtained from Sigma Chemical Company, St. Louis, Mo., USA) were washed twice with two volumes of saline using a glass fritted funnel. The enzyme-coated beads were added to the transfeirrin solution at a proportion of 6.0 mLU of neuraminidase per mg of transferring, and the slurry was allowed to mix at 37° C. for approximately 4 hours in an environmental chamber. The reaction was terminated by filtration to remove the beads, and sufficient 10N NaOH was added to the resulting solution to raise the pH to 8.0. The concentration of CDT in the resulting solution was determined by %CDT TURBIDIMETRIC IMMUNOASSAY, an assay kit commercially available from Bio-Rad Laboratories, Inc., Hercules, Calif., USA.

3. Preparation of the Base Matrix

Units of normal human plasma were pooled and defibrinated by conventional procedures known and used in the art. The total protein concentration of the resulting serum base matrix was adjusted to 6.0 g/dL by concentrating the base matrix or diluting it with physiological saline solution as necessary. The endogenous CDT and transferring levels in the base matrix were then determined by conventional techniques.

4. Preparation of the Reference

Appropriate volumes of the CDT solution prepared in Section 2 above were added to volumes of the base matrix prepared in Section 3 to achieve references with graduated levels of CDT. Thus, to prepare one liter of a 3% CDT reference, the base matrix alone (one liter) was used; to prepare one liter of a 6% CDT reference, 15 mL of the CDT solution was added to 985 mL, of the base matrix; and to prepare one liter of a 9% CDT reference, 30 mL of the CDT solution was added to 970 mL of the base matrix. Any adjustments needed to achieve the target concentrations were made by adding either additional CDT solution or additional base matrix. Once the solutions were combined, antimicrobial and stabilizing agents were added, and the resulting solutions were mixed for thirty minutes at room temperature, sterile filtered, and aseptically placed in sterile glass vials using sterile stoppers. The solutions were then stored at 2–8° C.

5. Sensitivity of the Product to Test Variances

Three CDT solutions (nominally 3%, 6% and 9% normalized to the total transferring concentration) were prepared as indicated in the preceding section, and each was analyzed for its weight percent CDT and mg/dL total transferring using the % CDT TURBIDIMETRIC IMMUNOASSAY. Ten repetitions were performed on each test to detect the sensitivity of each solution to test and analytical variances. The results, in terms of the mean, the standard deviation (SD) and the percent coefficient of variation (% CV) for each level, are listed in the table below.

| | Variations in Repeat Testing | | | | | | | | |
|---|---|---|---|---|---|---|---|---|---|
| | Level 1 | | | Level 2 | | | Level 3 | | |
| Analyte | Mean | SD | % CV | Mean | SD | % CV | Mean | SD | % CV |
| CDT (%) | 3.45 | 0.26 | 7.53 | 5.99 | 0.09 | 1.50 | 8.46 | 0.83 | 9.81 |
| Transferrin (mg/dL) | 282.02 | 18.51 | 6.56 | 250.78 | 8.29 | 3.31 | 370.92 | 21.22 | 5.72 |

Values of CV that are typically encountered in commercially available tests for both normal and abnormal samples are approximately 4%. The data presented above demonstrate that the solutions of CDT at target levels are of comparable sensitivity.

6. Closed-Vial Stability of the Product

Separate closed vials of the product at the three CDT levels used in the preceding sections were stored at 35° C., 41° C., and 47° C., in an accelerated shelf life test for periods of time that would be equivalent to storage at 2–8° C. for two-year periods, according to an Arrhenius model for correlating performance at the higher temperature with that at the lower temperature. The % CDT determinations were performed with the same test kits as in the preceding sections, and the results indicated that each product remained stable at the elevated temperatures for the shortened time periods and would therefore remain stable at 2–8° C. for at least two years.

In a separate test, closed vials of the product at the same three CDT levels were stored at 2–8° C. to provide real-time stability information. The CDT concentrations were determined at six points in time (using the assay kit described above) throughout the test duration of approximately 235 days, and are plotted in FIG. 1. In this plot, level 1 is indicated by diamond-shaped data points, level 2 by square-shaped data points, and level 3 by triangle-shaped data points. These results clearly show that the products were stable up to at least 235 days.

7. Open-Vial Stability of the Product

Open-vial stability tests were performed to simulate actual use conditions in a clinical laboratory. These tests were performed on products at the same three CDT levels as the closed-vial stability tests, in the same manner, except that the test lasted thirty days and once each day the vials were removed from storage (at 2–8° C.) and allowed to equilibrate to room temperature fore fifteen minutes, then opened and their contents exposed to the laboratory environment, then reclosed and returned to storage at 2–8° C.

Figure 2:
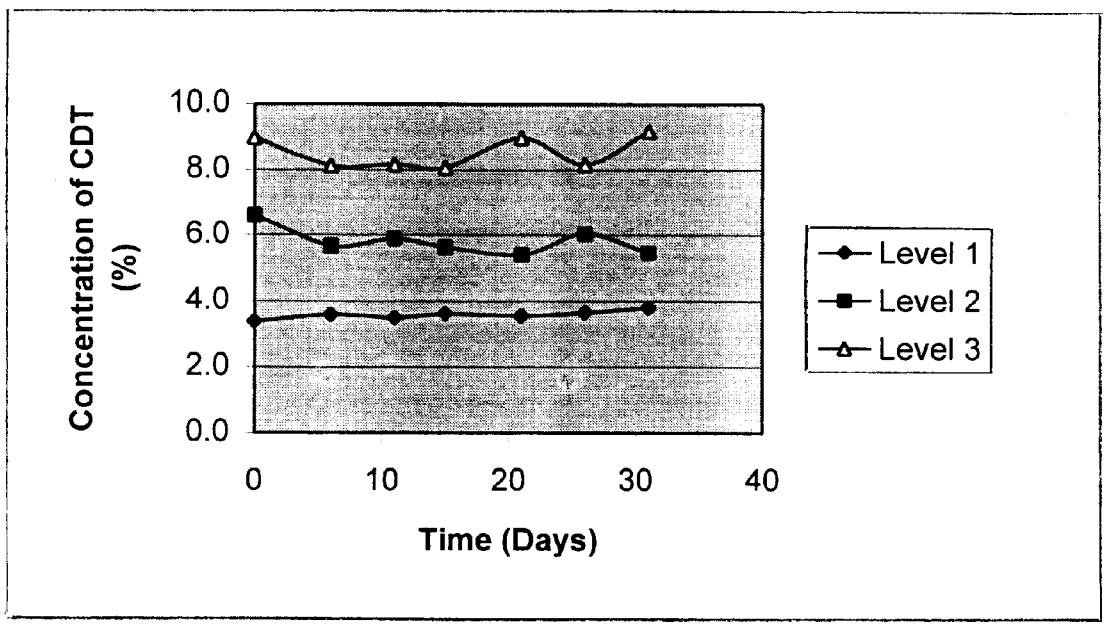
FIG. 2 is another plot of measured percent CDT concentration as a function of time for three CDT reference solutions prepared in accordance with this invention, this plot providing an indication of the stability of the solutions in open vials.

The CDT concentrations were determined at six points in time (using the assay kit described above) over the thirty-day test period, and are plotted in FIG. 2. In this plot, level 1 is indicated by diamond-shaped data points, level 2 by square-shaped data points, and level 3 by triangle-shaped data points. These results clearly show that the products were stable through at least 30 days.

The foregoing is offered primarily for purposes of illustration. Further modifications and variations that fall within the scope of the invention will be readily apparent to those skilled in the art.

What is claimed is:

1. A method for preparing a fluid containing carbohydrate-deficient transferring at a preselected concentration for use as a reference in determinations of carbohydrate-deficient transferring (CDT) levels in human bodily fluids in which elevated levels of CDT are an indication of chronic overconsumption of alcoholic beverages, said method comprising:

(a) contacting a fluid selected from the group consisting of a transferring-containing human bodily fluid and a transferring-containing fraction of a human bodily fluid with a neuraminidase thereby causing digestion of a majority of transferring in said fluid to CDT by said neuraminidase, (b) recovering said fluid from said neuraminidase, (c) quantifying the amounts of CDT and transferring remaining in said fluid, and (d) combining said recovered fluid with a matrix human bodily fluid having known CDT and transferring levels in order to create said reference with known CDT and transferring levels.

2. A method in accordance with claim 1 in which said fluid of (a) is a member selected from the group consisting of blood, serum, plasma, cerebrospinal fluid, and fractions thereof.

3. A method in accordance with claim 1 in which said fluid of (a) is a fraction of a member selected from the group consisting of serum and plasma.

4. A method in accordance with claim 1 in which said fluid of (a) is Cohn Fraction IV.

5. A method in accordance with claim 1 in which said neuraminidase is from Clostridium spp.

6. A method in accordance with claim 1 in which said neuraminidase is from *Clostridium perfringens*.

7. A method in accordance with claim 1 in which step (a) is performed under conditions that produce a solution in which said carbohydrate-deficient transferring is at least about 75% by weight of all transferring therein.

8. A method in accordance with claim 1 in which step (a) is performed under conditions that produce a solution in which said carbohydrate-deficient transferring is at least about 85% by weight of all transferring therein.

9. A method in accordance with claim 1 in which said neuraminidase is immobilized on a solid support.

10. A method in accordance with claim 9 in which said solid support is comprised of microparticles.

11. A method in accordance with claim 1 in which step (a) is performed at a pH of from about 4.5 to about 5.5.

12. A method in accordance with claim 1 in which said fluid of step (a) contains transferrin at a concentration of at least about 300 mg/dL.

13. A method in accordance with claim 1 in which said fluid of step (a) contains transferring at a concentration of at least about 1,000 mg/dL.

14. A method in accordance with claim 1 in which said matrix human bodily fluid of step (d) is a member selected from the group consisting of blood, serum, plasma, and cerebrospinal fluid.

15. A method in accordance with claim 1 in which said matrix human bodily fluid of step (d) is serum.

16. A method in accordance with claim 1 further comprising adding an antimicrobial agent to said combination of recovered fluid and matrix human bodily fluid.

17. A method in accordance with claim 1 further comprising adding a stabilizing agent to said combination of recovered fluid and matrix human body fluid.

* * * * *